US 9,387,492 B2

(12) United States Patent
Leen et al.

(10) Patent No.: US 9,387,492 B2
(45) Date of Patent: Jul. 12, 2016

(54) LIQUID DROPLET DISPENSER

(75) Inventors: Gabriel Leen, Cork (IE); Bernard Bryce, Corofin (IE)

(73) Assignee: UNIVERSITY OF LIMERICK, Limerick (IE)

( * ) Notice: Subject to any disclaimer, the term of this patent is extended or adjusted under 35 U.S.C. 154(b) by 111 days.

(21) Appl. No.: 13/820,273

(22) PCT Filed: Sep. 7, 2011

(86) PCT No.: PCT/IE2011/000048
§ 371 (c)(1),
(2), (4) Date: Mar. 1, 2013

(87) PCT Pub. No.: WO2012/032503
PCT Pub. Date: Mar. 15, 2012

(65) Prior Publication Data
US 2013/0153677 A1 Jun. 20, 2013

(30) Foreign Application Priority Data
Sep. 7, 2010 (IE) .................................. 2010/0544

(51) Int. Cl.
*B05B 1/08* (2006.01)
*B05B 1/00* (2006.01)
*B01L 3/02* (2006.01)
*B05B 17/06* (2006.01)
*G01N 35/10* (2006.01)

(52) U.S. Cl.
CPC ................ *B05B 1/00* (2013.01); *B01L 3/0268* (2013.01); *B05B 17/0607* (2013.01); *G01N 35/1009* (2013.01); *B01L 2200/146* (2013.01); *B01L 2300/0832* (2013.01); *B01L 2400/0439* (2013.01); *B01L 2400/0481* (2013.01); *G01N 2035/1034* (2013.01); *G01N 2035/1048* (2013.01)

(58) Field of Classification Search
CPC ............ B05B 17/0646; B05B 17/0615; B05B 17/063; B05B 17/06; A61L 9/14; A61L 2209/132; A61L 2209/13; A61K 2800/87; B01L 3/0268; B01L 2200/146; B01L 2300/0832; B01L 2400/02; B01L 2400/0439
USPC ............................................ 239/102.1, 102.2
See application file for complete search history.

(56) References Cited

U.S. PATENT DOCUMENTS

| 4,115,789 A | | 9/1978 | Fischbeck |
| 4,769,009 A | * | 9/1988 | Dykstra ................. 604/155 |
| 5,248,087 A | * | 9/1993 | Dressler ............... 239/102.2 |

(Continued)

FOREIGN PATENT DOCUMENTS

WO          97/44134          11/1997

*Primary Examiner* — Len Tran
*Assistant Examiner* — Adam J Rogers
(74) *Attorney, Agent, or Firm* — Jacobson Holman, PLLC.

(57) ABSTRACT

An apparatus for dispensing droplets comprises a dispensing tip with an orifice having a cross sectional area in the range of 0.00002 mm2 to 0.03 mm2. An actuator assembly comprising an actuator element engages with and disengage from the tip and, when engaged, couples acoustic energy to liquid in the tip to expel the liquid through the orifice as a droplet. The actuator assembly includes one or more piezo elements, which may be in the form of piezo stacks. In some embodiments, the actuator assembly comprises a plurality of jaws adapted to move to engage with the dispensing tip for dispensing. This allows side loading of the tip followed by movement of the actuator assembly to engage the tip.

18 Claims, 15 Drawing Sheets

(56) References Cited

U.S. PATENT DOCUMENTS

| | | |
|---|---|---|
| 6,070,779 A | 6/2000 | Baggerman |
| 6,387,330 B1 | 5/2002 | Bova |
| 6,861,034 B1* | 3/2005 | Elrod et al. .................... 422/501 |
| 7,585,463 B2* | 9/2009 | Austin et al. .................... 422/63 |
| 8,057,756 B2* | 11/2011 | Londo et al. .................. 422/501 |
| 8,273,307 B2 | 9/2012 | Eickhoff |
| 2001/0036424 A1* | 11/2001 | Takahashi et al. ............. 422/100 |
| 2006/0210443 A1* | 9/2006 | Stearns et al. ................. 422/100 |
| 2007/0269348 A1 | 11/2007 | van den Engh |
| 2008/0227663 A1* | 9/2008 | Tisone et al. .................... 506/39 |
| 2011/0180622 A1* | 7/2011 | Selby .................. B05B 17/0646 239/102.2 |
| 2013/0206857 A1* | 8/2013 | Ivri ................................... 239/4 |
| 2014/0091155 A1* | 4/2014 | Jordan ............... B05B 17/0669 239/4 |

* cited by examiner

280

285

290

_LIQUID DROPLET DISPENSER_

This is a national stage of PCT/IE11/000048 filed Sep. 7, 2011 and published in English, which has a priority of Irish no. 2010/0544 filed Sep. 7, 2010, hereby incorporated by reference.

FIELD OF THE INVENTION

The invention relates to dispensing of liquids in small volumes, including small droplets, in the nano and pico liter size ranges.

There are several application areas in which it is desired that very small droplets be accurately and reliably dispensed by means of a non-contact drop-on-demand dispenser. These fields include for example the biomedical, proteomics, systems biology, pharmacology, and diagnostics fields. The invention may also be applied in industrial applications such as the dispensing of adhesives, lubricants, coatings and inks.

PRIOR ART DISCUSSION

It is known to bond a piezo element to a tip near the orifice of a dispenser. Because of this bond, the sub-micron vibrations (pressure waves) of the piezo element are transferred to the liquid, causing drops to be ejected from the orifice. Examples disclosed in DE102005025640, WO97/44134, and U.S. Pat. No. 6,070,779.

The requirement to bond the piezo actuator element to the tip results in manufacture being expensive. Also, there is an onerous requirement to ensure that there are no voids in the bonding cement, as such voids would potentially impair performance and repeatability. This requirement also means that the tip is not separable from the piezo actuator element.

The invention is directed towards achieving an improved dispensing apparatus a for non-contact droplet dispensing. A particular objective is to achieve greater versatility and lower cost, while achieving good accuracy.

SUMMARY OF THE INVENTION

According to the invention, there is provided a dispensing apparatus for dispensing droplets, the apparatus comprising:
- a dispensing tip having a fluid passage with an orifice, said orifice having a cross sectional area in the range of 0.00002 $mm^2$ to 0.03 $mm^2$, and
- an actuator assembly comprising an actuator element and being arranged to engage with and disengage from the tip and, when engaged, to couple acoustic energy to liquid in the fluid passage to expel said liquid through the orifice as a droplet.

In one embodiment, the actuator assembly includes one or more piezo elements, which may be in the form of piezo stacks.

In one embodiment, the actuator assembly comprises a plurality of jaws adapted to move to engage with the dispensing tip for dispensing.

In one embodiment, the apparatus is adapted to allow side loading of the tip followed by movement of the actuator assembly to engage the tip.

In one embodiment, the actuator assembly comprises an interface for contacting the dispensing tip and for transferring acoustic energy from the actuator element to the tip.

In one embodiment, the actuator assembly is adapted to apply a static mechanical pressure against the tip, said static mechanical pressure being a bias force upon which the actuator applies a pressure wave.

In one embodiment, the actuator assembly comprises an inertial mass for the actuator element to act against in order to couple pressure waves into the dispensing tip.

In one embodiment, the tip is a friction fit into the actuator assembly.

In one embodiment, the actuator assembly has a contact surface inclined in cross-section to an axis of the tip at an angle in the range of 0° to 5° and preferably 1° to 1.5°.

In one embodiment, the actuator assembly comprises an opening into which the dispensing tip fits with axial movement.

In one embodiment, the actuator assembly comprises a mechanism for amplifying actuator element movement.

In one embodiment, said mechanism comprises a base and a pivoting link arm one end of which is acted upon by the actuator element and the other end of which has a face for engagement with the tip.

In one embodiment, the actuator assembly is adapted to provide controlled heating in the region of the orifice only.

In one embodiment, the dispensing tip is adapted for storage of liquid before dispensing.

In one embodiment, the dispensing tip is in a funnel configuration, having an upper reservoir and a lower liquid-containing portion having the orifice.

In one embodiment, the cross-sectional area of the lower liquid-containing portion is in the range of about 0.01 $mm^2$ to 81 $mm^2$.

In one embodiment, the lower portion of the dispensing tip has an angle to axial taper angle in the range of 0° to 5°, and more preferably in the range of 1° to 1.5°.

In one embodiment, the inner surface of the tip at the orifice is funnel-shaped, extending inwardly and downwardly, and bending downwardly to a smaller angle to axial at the orifice.

In one embodiment, the tip is adapted so that it can be fitted to a standard pipette to allow the dispensing of drops when inserted into a suitable head assembly.

In one embodiment, the dispensing tip further comprises a means of venting and connection to a pressure control system.

In one embodiment, the dispensing tip has a membrane which may be punctured for use.

In one embodiment, the material of the dispensing tip is polypropylene.

In one embodiment, the tip has a hydrophobic coating around the orifice.

In one embodiment, the apparatus further comprises a conduit for supplying liquid from a container to the tip.

In one embodiment, the apparatus further comprises a sensor arranged to sense liquid dispensing from the dispensing tip, a controller, a controller, and feedback means in the controller for dynamically controlling the actuator assembly in response to sensing of liquid dispensing.

In one embodiment, the controller is adapted to control pressure of liquid in the tip in response to said sensing.

In one embodiment, the sensor comprises a camera.

In one embodiment, the sensor comprises an infra-red sensor.

In one embodiment, the controller is adapted to control the temperature of liquid in the tip in response to said sensing.

In one embodiment, the system is a biomedical liquid dispensing system.

In one embodiment, the system is a liquid adhesive dispenser.

In one embodiment, the apparatus further comprises a heater to heat bulk phase change liquid in the tip.

In one embodiment, the apparatus further comprises means to apply a positive back pressure to space within the tip to provide a continuous flow of liquid from the orifice, and the actuator assembly is adapted to apply acoustic energy to break said stream.

In one embodiment, the controller is adapted to control the apparatus with the steps of applying:
- negative liquid back pressure to prevent dripping,
- positive liquid back pressure to blow out a small quantity of liquid,
- negative liquid back pressure, and
- acoustic energy pulses to the dispensing tip to create pressure waves for droplet dispensing.

In another aspect, the invention provides a liquid dispensing method performed with a dispensing apparatus of any preceding claim, the method comprising the steps of providing a liquid in the dispensing tip and operating the actuator assembly to cause drops to exit the dispensing tip orifice.

In one embodiment, a primer liquid which is immiscible with a liquid of interest is contained in the tip and is flushed or dispensed through the tip orifice before dispensing of the liquid of interest.

In one embodiment, there are primer liquids below and above the liquid of interest.

In a further aspect, the invention provides a dispensing tip comprising a liquid-containing body with a lower fluid passage having an external surface for engaging an actuator assembly and an orifice having a cross sectional area in the range of 0.00002 mm$^2$ to 0.03 mm$^2$.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

A dispensing apparatus of the invention has a dispensing tip containing liquid to be dispensed, the tip being brought into contact with an actuator assembly which applies acoustic waves to the liquid to cause droplet dispensing, and the tip is then removed. The apparatus has some or all of the following advantages over the prior art:
- more accuracy, and/or
- reduced minimum volume of liquid necessary for dispensing, and/or
- ability to reliably dispense small volumes, and/or
- reduced risk of contamination, and/or
- quick change over of liquids to be dispensed due to interchangeability of the tip, and/or
- ability of the tip to act as a fluid container (or ability to dispense directly from supplied container) and/or
- more reliability, and/or
- low cost.

Figure 1:
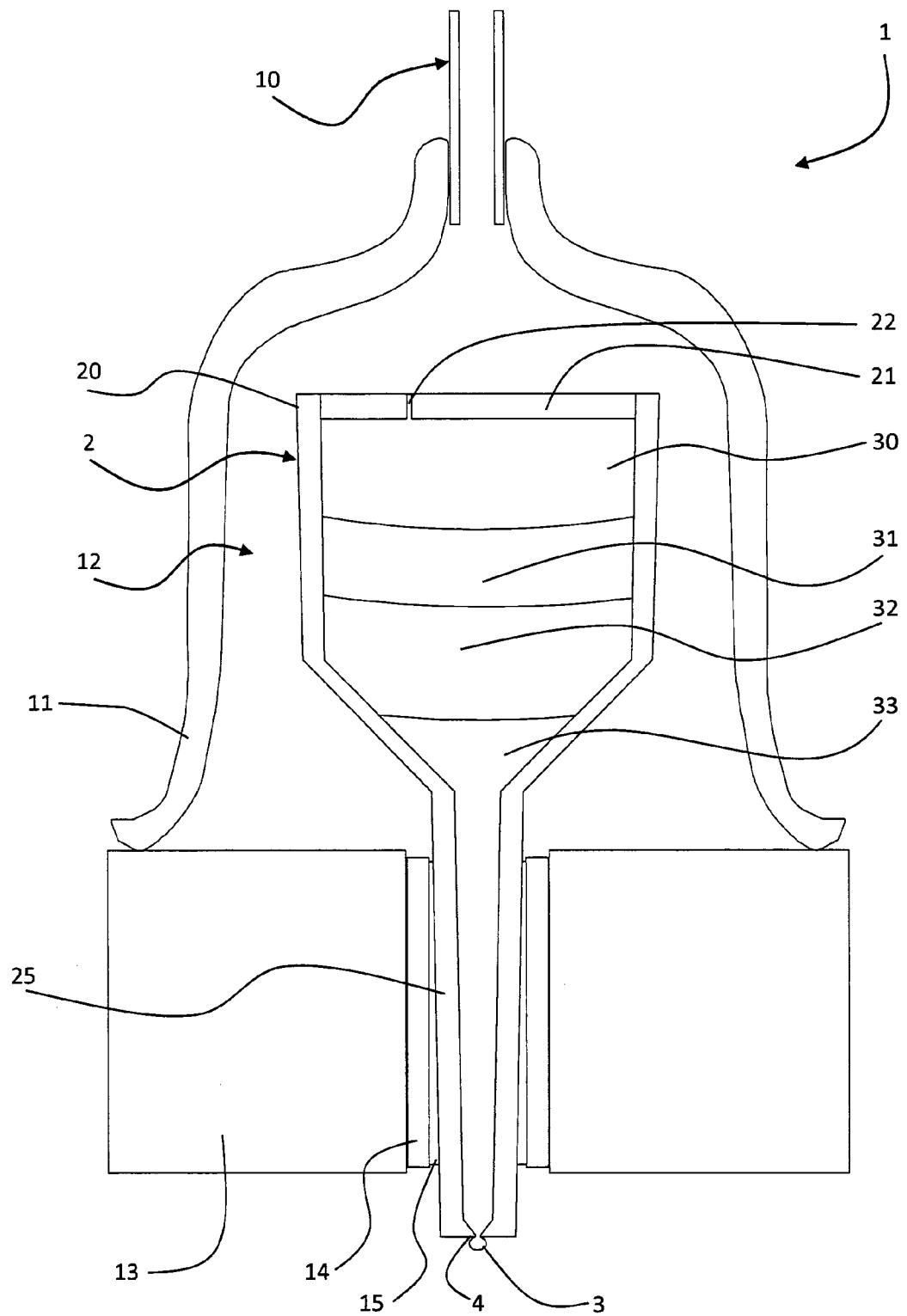
FIG. 1 is a cross-sectional diagram illustrating a dispensing head of the invention.
Figure 2:
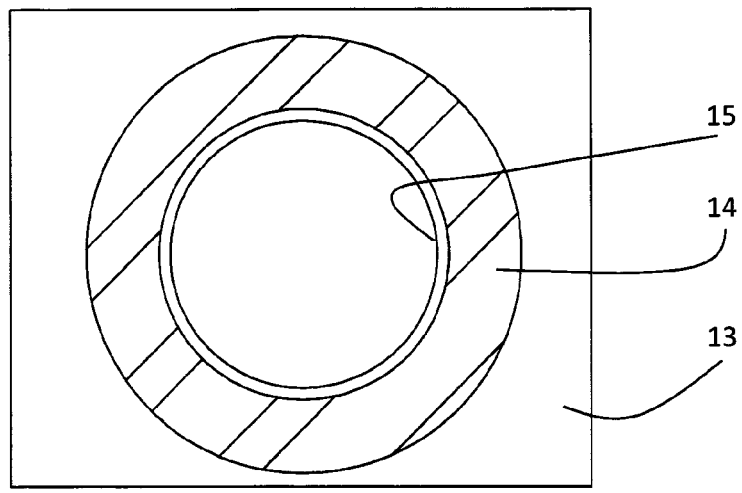
FIG. 2 is a more detailed cross-sectional view through a cylindrical/tubular piezo actuator of the dispensing head.
Figure 2:
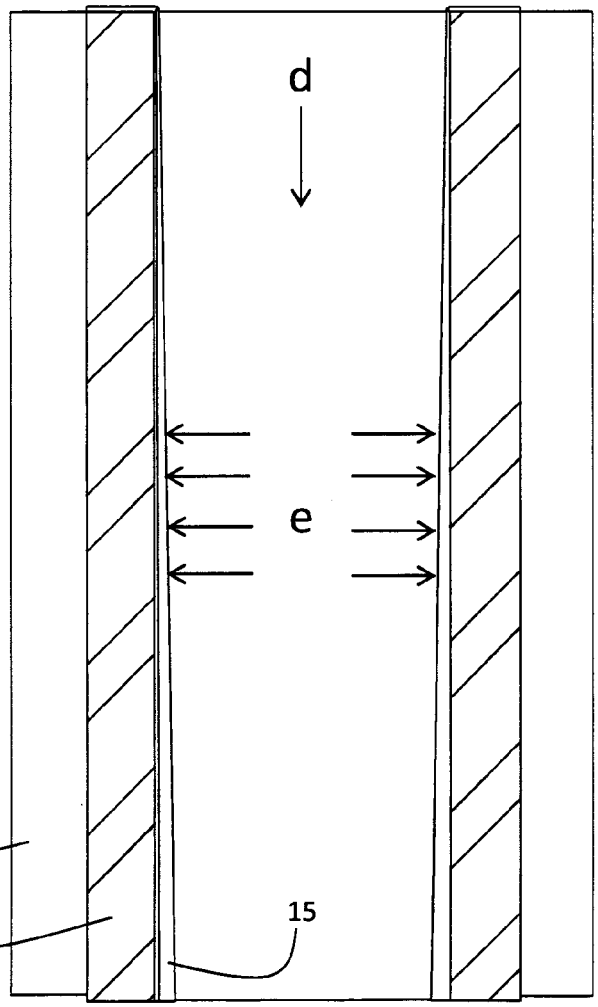

Referring to FIGS. 1 and 2 a dispensing apparatus 1 of the invention comprises a changeable dispensing tip 2. The tip 2 contains a small volume of one or more liquids. It can be inserted into an actuator assembly for a single use or the tip may be removed, while still containing fluid, and stored for later reinsertion and use. It is configured for very accurate dispensing of a small droplet 3 at its orifice 4. Because the dispensing tip 2 is changeable and can be made from plastics material, it is inexpensive as an actuator dedicated and bonded to each individual tip is not required. Furthermore, because the dispensing tips are changeable and potentially disposable, then the risk of sample cross-contamination is avoided. For example, the tip can be used to dispense once or several times, into a 96 well plate, (or onto a micro array substrate) and then discarded.

In this embodiment, the apparatus 1 further comprises a vacuum tube 10 and a vacuum seal 11 creating a vacuum chamber 12 over a block 13. The block 13 supports a piezo element 14 and a conical interface 15 between the piezo element 14 and the dispensing tip 2. The tip 2 can be inserted and removed, as it is not bonded to the interface 15.

The dispensing tip 2 comprises a top portion 20 of large cross-sectional area at the top of which there is a lid 21 with a vent 22. In this example use the dispensing tip 2 contains:
- 30, air at the same pressure as the chamber 12;
- 31, an upper priming liquid;
- 32, liquid to be dispensed; and
- 33, lower priming liquid.

A smaller cross-sectioned bottom portion 25 terminating in the orifice 4.

The function of the vent 22 is to allow the air pressure at the back of the tip 2 to be controlled. This gives a way to control the liquid pressure at the orifice relative to atmosphere, to establish and maintain a working meniscus. Regulation of correct pressure via a pressure control system is advantageous. The air 30 is at the same pressure as in the chamber 12, due to the vent 22.

FIG. 2 shows how the tip 2 is inserted in the direction of the arrow "d" and due to the taper in the interface 15 presses out in the directions of the arrows "e". There is a taper angle in the range of close to 0° and up to 5°. FIG. 2 also shows a cut section of the piezo element 14 with a conical section, in this one particular embodiment.

For a conical insert and matching actuator, the static force of the actuator walls on the dispensing tip is proportional to the insertion force, and inversely proportional to the sine of the taper angle.

$$F \alpha f \sin^{-1}(\theta).$$

Whether or not the dispensing tip is manually inserted or machine inserted, or indeed whether it will be kept in place by frictional forces between the insert wall and the actuator, or kept in place by a keeper which exerts a continuous force in it, will be dependent on the specific application and embodiment. The embodiment in FIG. 2 uses a dispensing tip which keeps itself in place by friction. It is anticipated that it will be possible to use a larger taper angle if the insert is to be held down into the actuator by a keeper, or indeed there may be no taper.

There is a conical section 15 to match the conical shape of the outside of the dispensing tip. The piezo element 14 is a commercially available cylindrical piezo element which expands and contracts radially. It comprises a ceramics sleeve-shaped body plated internally and externally with electrodes. The dispensing tip is inserted with a force in direction 'd'. When the tip is in place it remains there by frictional forces. It now presses against the conical section 15 with a force in direction 'e'. This positive static pressure exerted in an outward direction by the tip on the conical section enables the piezo actuator to couple the pressure waves into the tip (through the cast section).

The interface 15 has a slope, in this example, of 1.35° included angle θ (i.e. 0.625° per side). This works well for a closed cylindrical piezo element, with the observation that the tip, when inserted, will hold itself in place by friction. However it shows resistance to removal, and the position where the piezo squeezes it is largely dependant on how firmly it is pressed into the piezo. However, as shown in further embodiments below it is not essential that there be a taper. For example opposing jaws may move radially to grip the tip.

Figure 3:
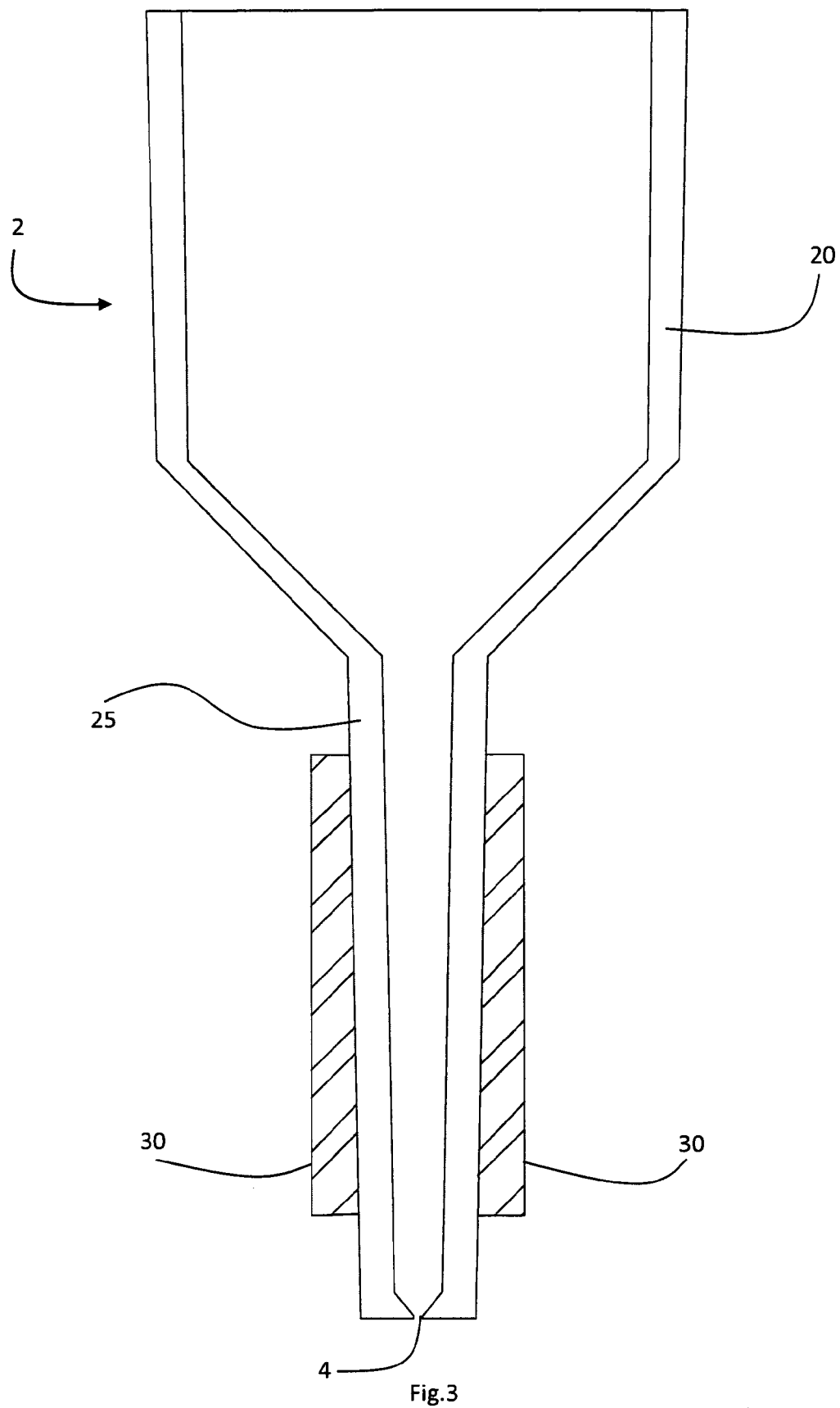
FIG. 3 is a diagram showing a specific configuration of disposable dispensing tip and a piezo element for one embodiment.

FIG. 3 shows an actuator assembly 30 having an actuator element integrated with an interface material.

Figure 4:
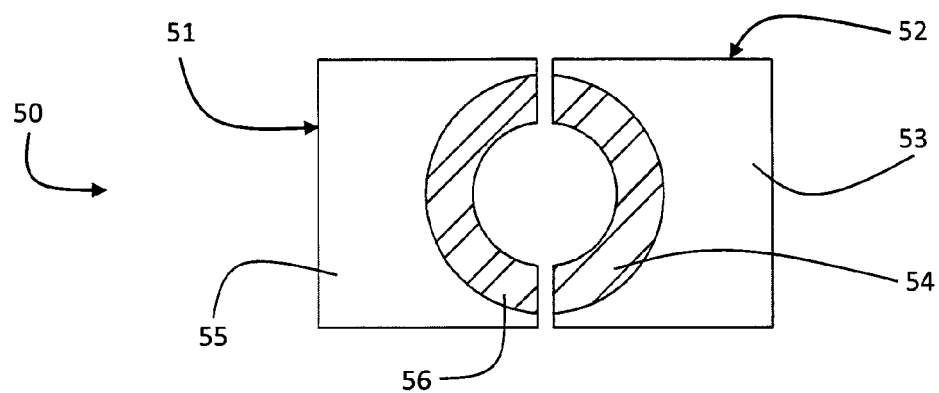
FIGS. 4 and 5 are cross-sectional views of an alternative actuator and the manner of loading a tip into it.
Figure 5:
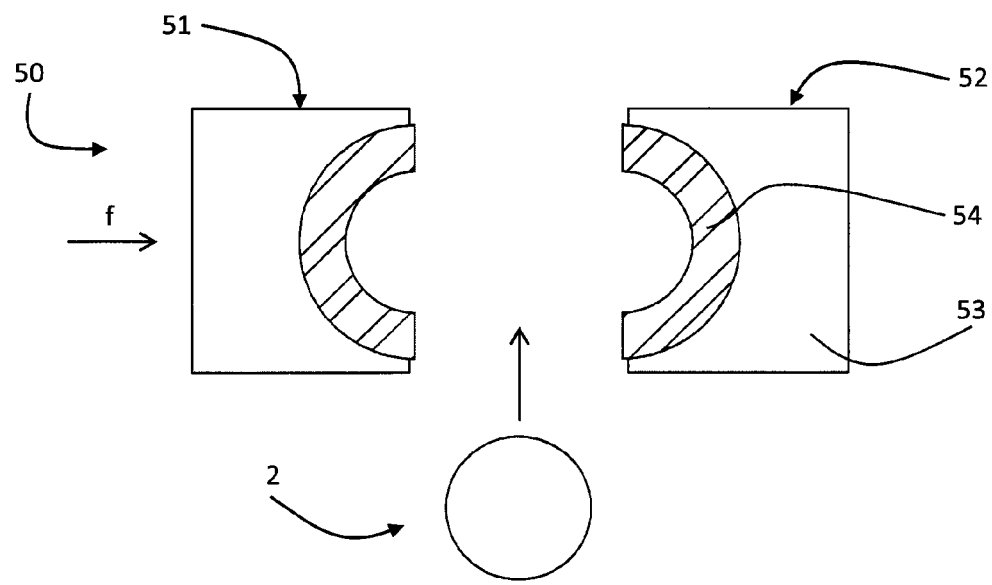
Figure 7:
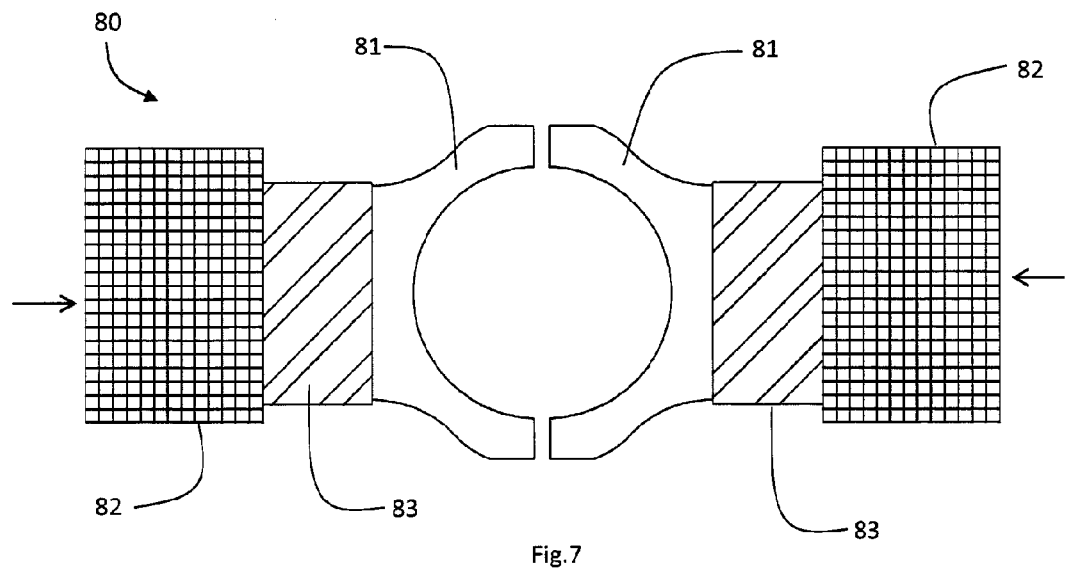
Figure 8:
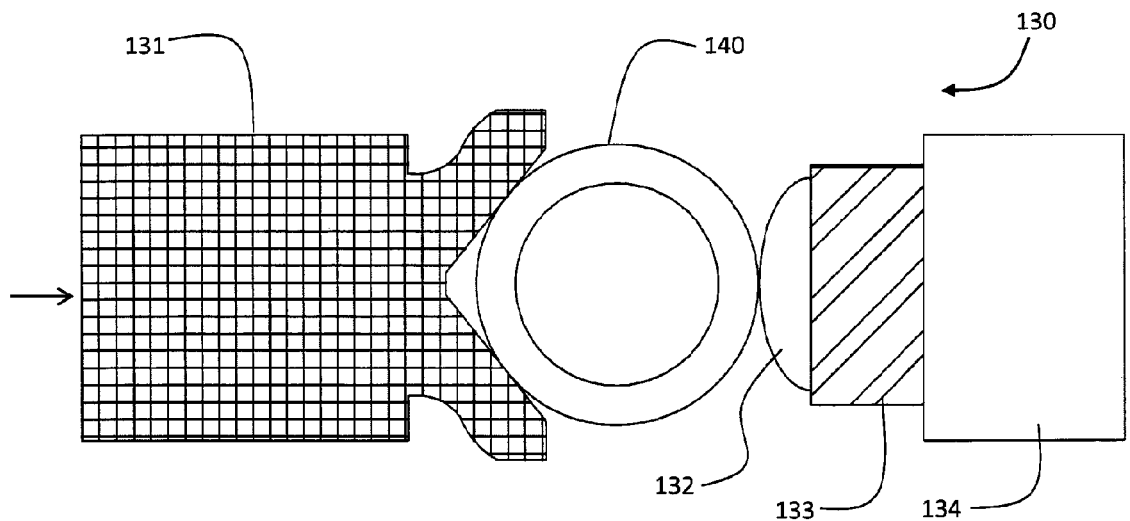

FIGS. 4 and 5 show a split actuator assembly 50 configuration having two halves 51 and 52, which form jaws which open for the tip stem 2 to be loaded from the side. The half 52 has a block 53 and a piezo element 54, and the half 51 has a block 55 and a piezo element 56. In FIG. 5 there is a configuration using a split actuator assembly piezo cylinder and holder), which can be opened to take the tip. This allows the dispensing tip to be inserted and removed sideways. Because in FIGS. 4 to 8 the piezo and holder are split into pieces (or "jaws"), the holder is opened and the tip is inserted from the side. The holder is closed with a retaining force (for example in directions of the arrows (FIG. 5, 7 or 8). This retaining force maintains the desired positive static pressure between the piezo and the dispensing tip.

Figure 6:
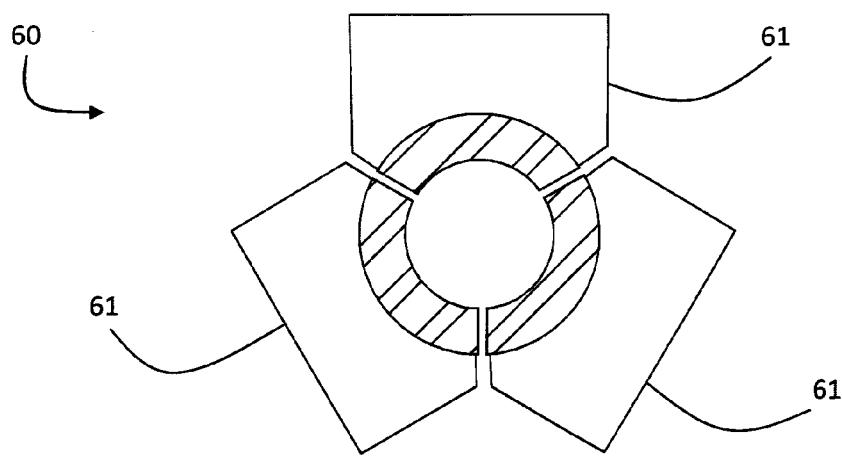
FIGS. 6 to 9 are various views of alternative dispensing head arrangements.

FIG. 6 shows an actuator assembly 60 with three jaws 61 at 60° to each other, with centres at 120° and arranged in a concentric pattern to couple around the dispensing tip stem. In this case additional piezos may be used, to improve performance.

FIGS. 7 and 8 show a plan view of configurations using a block piezo component such as a piezo stack. In FIG. 7 an actuator assembly 80 has opposed jaws 81 which grip the tip stem and they are actuated by piezo elements 83 all mounted on blocks 82.

In FIG. 8 an actuator assembly 130 has a gripper 131 on one side, and on the opposed side there is a single convex gripper 132 on a piezo element 133, on a block 134. Again, the jaws/gripper may be moved to allow insertion of a dispensing tip, such that the tip may not only be loaded by insertion from the top but alternatively the tip may be inserted from the side and subsequently grasped by the actuation jaws/gripper.

These embodiments give the following advantages:

Allows the piezo to be closed tightly around the tip stem, in such a way that the tip and the actuator assembly are separable elements and not bonded with some form of adhesive to each other;

The dispensing heads may be loaded from the side and the dispensing tip orifice never comes in contact with any part of the dispensing head and thus the possibility of cross-contamination is much reduced. It should also be noted that many configurations of piezo transducer could be used, and indeed other electro mechanical actuators.

If a vertical split cylindrical actuator assembly is used, (e.g. FIG. 4, FIG. 5), where the actuator sections (the piezo cylinder is cut vertically to form two C-shaped sections) would close in around the inserted dispensing tip stem, a taper angle of zero degrees could be used in this case.

It is also envisaged that the fluid chamber section of the dispenser could be any convenient shape that allows sufficient energy to be transferred from the actuator(s) to the liquid to cause drop ejection at the orifice. This is particularly the case where piezo stack actuators are used with an interface between the piezo and the tip stem adapting the shape of the piezo to the shape of the wall of the tip stem and the tip stem is not bonded to the interface. Also, single or a multitude of actuators (acting together) of any suitable shape which are capable of generating and transferring energy to the corresponding fluid chamber could be used.

The drawings show how the actuator couples the pressure waves (energy) to the tip. In all cases there is positive static pressure between the actuator assembly and the tip (with or without an interface material).

Referring to FIG. 7, there are non-tubular actuators (in this case piezo stacks 83) with an interface material 81 which are in the form of jaws to couple the pressure waves from the piezo actuator 83 to the tip stem and into the liquid. A force is applied to the jaws 81 in directions of the arrows to close them around the tip, and to apply positive static pressure to it, to enable the pressure waves to couple easily. The actuator assembly also includes built-in bodies 82 each with a mass which has significant inertia (mass) relative to the actuators (and whatever they are moving).

The purpose of this inertia is for the actuator to act against, so that it transfers most of its energy into the tip. The mass can't move quickly and therefore holds one side of the actuator almost stationary. This increases the amount of movement at the working end of the actuator, and because the actuator is against a fixed inertia, it offers a stronger pressure pulse into the tip. The back end of the actuator has a controlled force and inertia (and/or possibly damping factor/friction).

For the cylindrical/tubular piezo actuator assembly of FIGS. 1 to 3 the clamping static pressure force is caused by the insertion force of the tip causing it to press against the walls, and no mass is necessary as the piezo expands and contracts radially as a complete unit.

Referring again to FIG. 8 the positive pressure is set in the direction of the arrow by the fixture 131 which can be removed to allow removal of the tip. The fixtures 134 and 131 have significant mass relative to the rapidly moving parts 132 and 133. In this case one of the actuators can be fixed in place and still exerts a positive static pressure on the tip and couples sufficient energy from the actuator element 133 into the liquid to dispense drops. The opposing fixture 131 need not be an active component, but a suitable mass, supplying the opposing static pressure. As illustrated, the shape of the interface material 132, need not necessarily be matched to the external profile of the tip.

Figure 9:
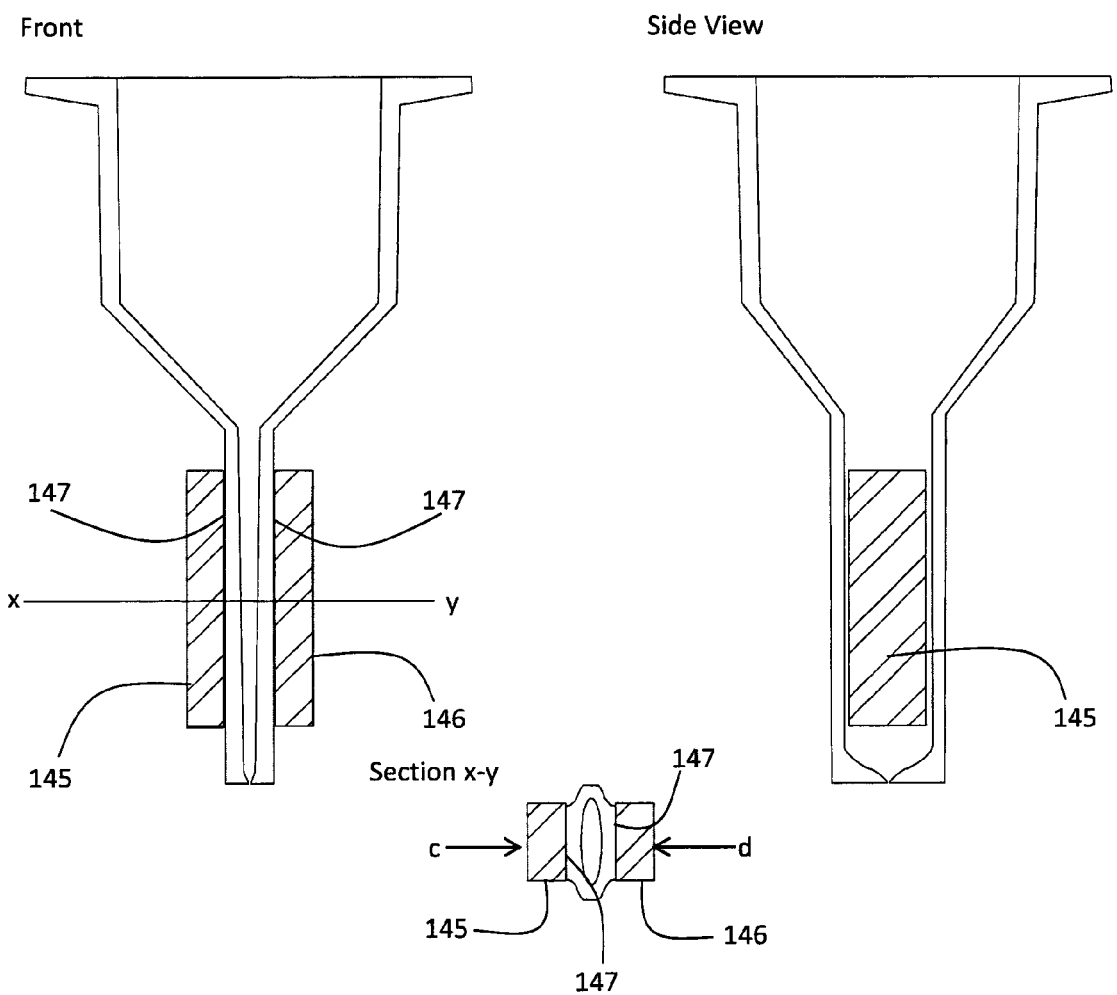

Also, several configurations are possible using different shaped actuators FIG. 9 shows rectangular shaped piezo actuators 145 and 146 and the tip stem has opposed flat faces 147 for contact with the flat actuators 145 and 146. Again, positive static pressure is important for the system to function.

Figure 10:
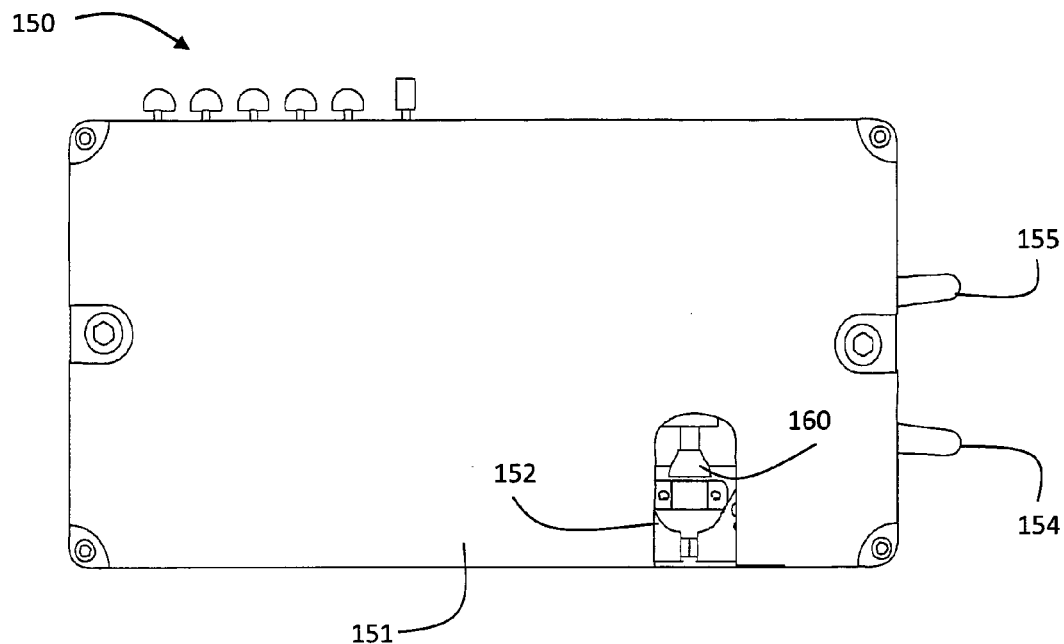
FIG. 10 is a front view of a dispensing apparatus.
Figure 11:
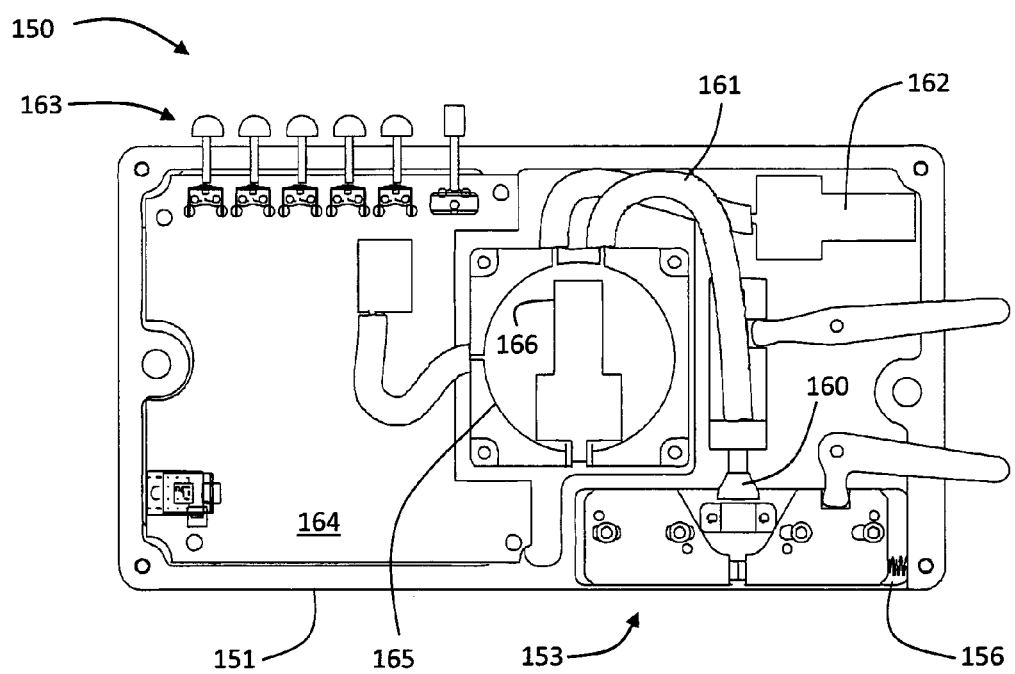
FIG. 11 shows the apparatus with the front cover removed, in which no dispensing tip is present.
Figure 12:
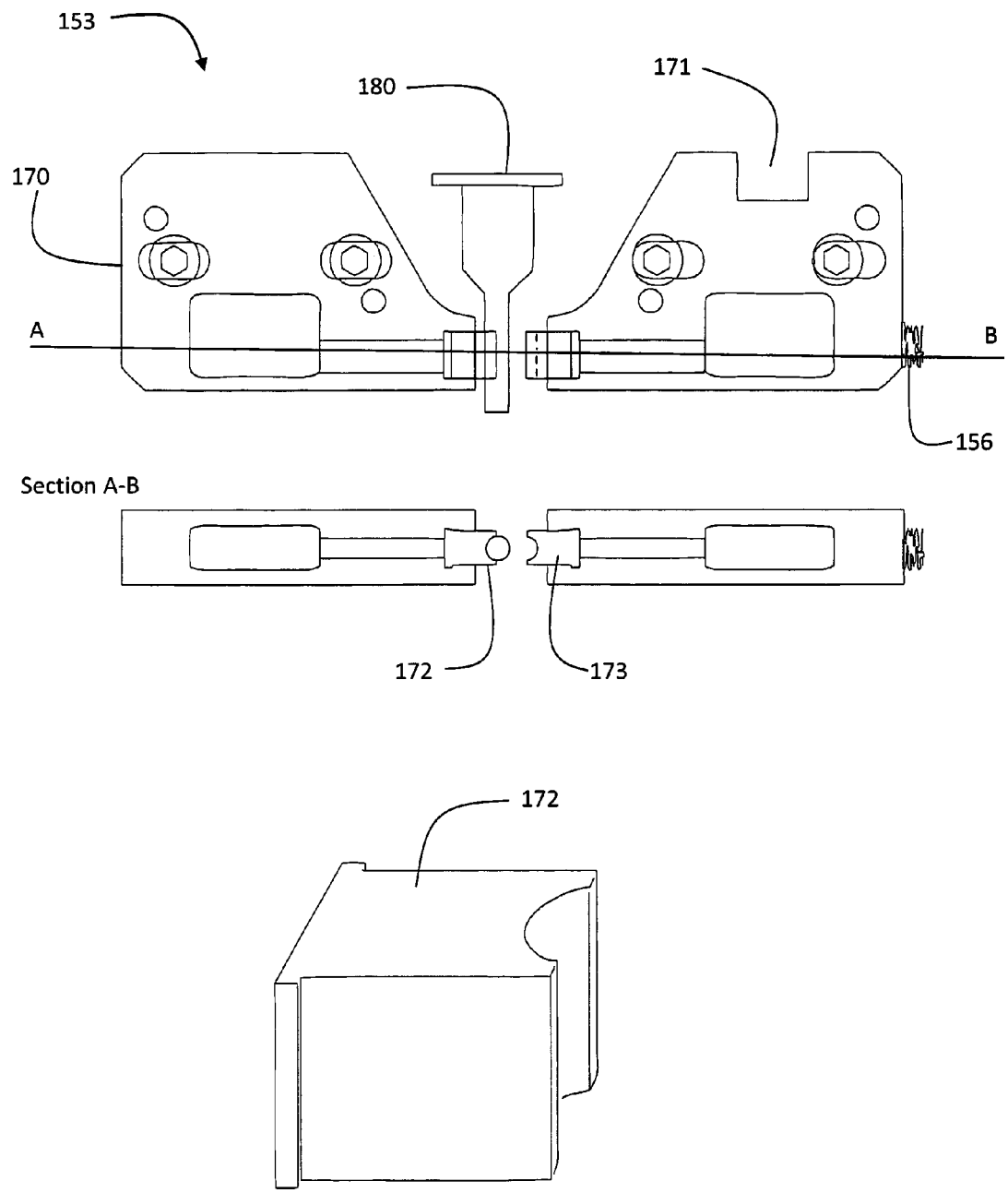
FIG. 12 shows an actuator of the apparatus in front and section views, and includes a perspective view of a jaw of the actuator, in which a dispensing tip is present in front and section views.

FIGS. 10 to 12 show an apparatus 150 having a housing 151 with an opening 152 in a front cover for side loading of a tip. There are jaws 172 and 173 for gripping any of a variety of tips, a control lever 154 to open and close the jaws 172 and 173, and a lever 155 to engage/disengage the pressure regulation system coupling. The right-hand jaw 172 of the actuator assembly 153 is biased by a spring 156 in order to apply a static holding pressure. A suction cup 160 is arranged to slide axially into and out of engagement with a tip by movement of the lever 155. There are vacuum tubes 161, a pressure pump 162, function keys 163, a circuit board 164, a vacuum control pump 166, and a vacuum chamber 165. The actuator jaw assembly 153, as shown in FIG. 12, has a fixed jaw 170 and a sliding jaw 171. A tip 180 is side-loaded and the lever 154 is operated to grip the tip 180. This arrangement (like that of FIG. 4, FIG. 5, FIG. 6, FIG. 7, FIG. 8, FIG. 9 and FIG. 12) avoids need for the tip and interface to be tapered. Interface components 172 and 173 are shown, which in this case have C-shaped profiles which match the outside profile of the dispenser tip stem. The dispensing tip 180 may be inserted into the actuation jaw assembly 153, or removed from the actuation jaw assembly 153, as is required.

Figure 13:
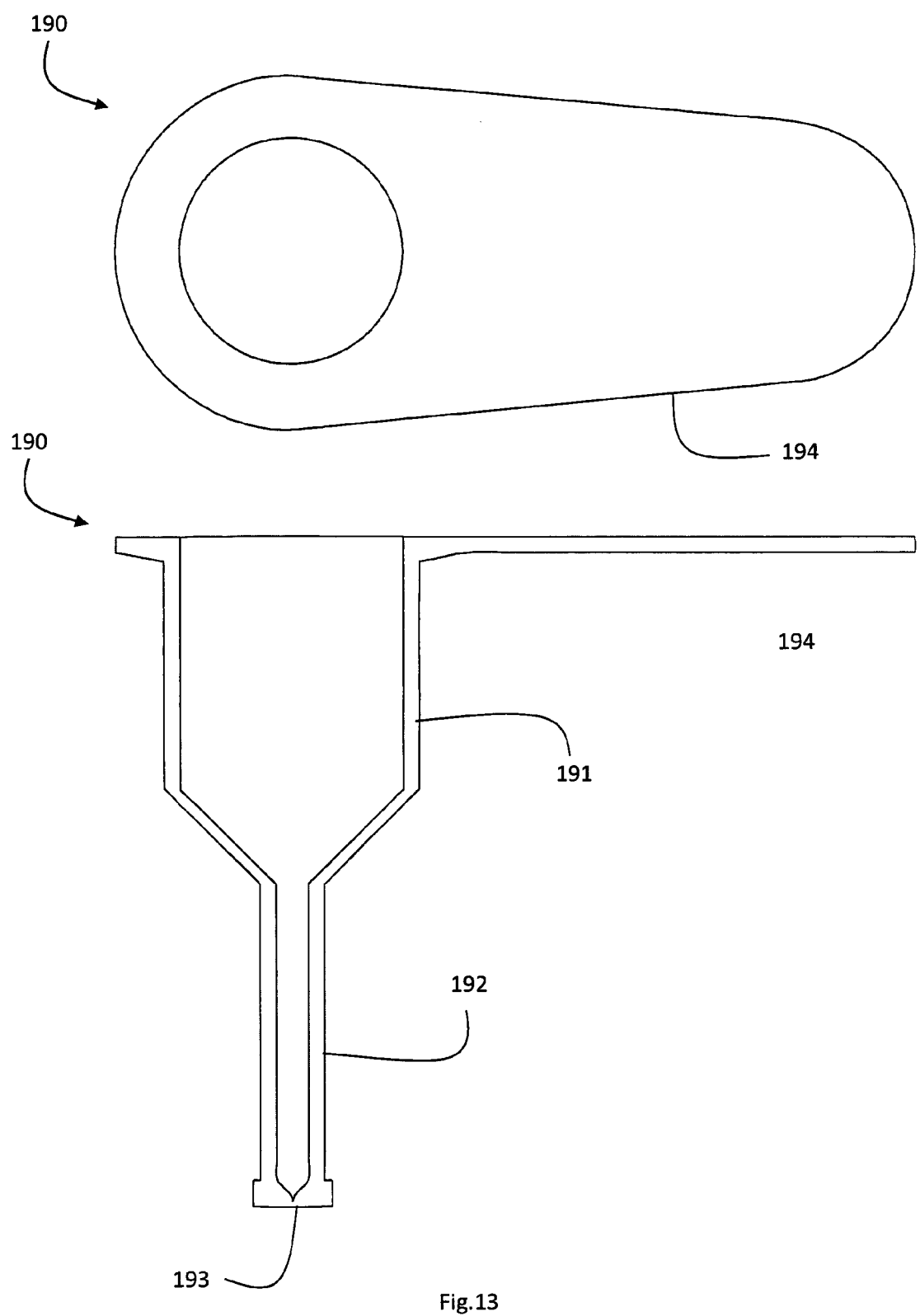
FIGS. 13 and 14 show dispensing tips.
Figure 14:
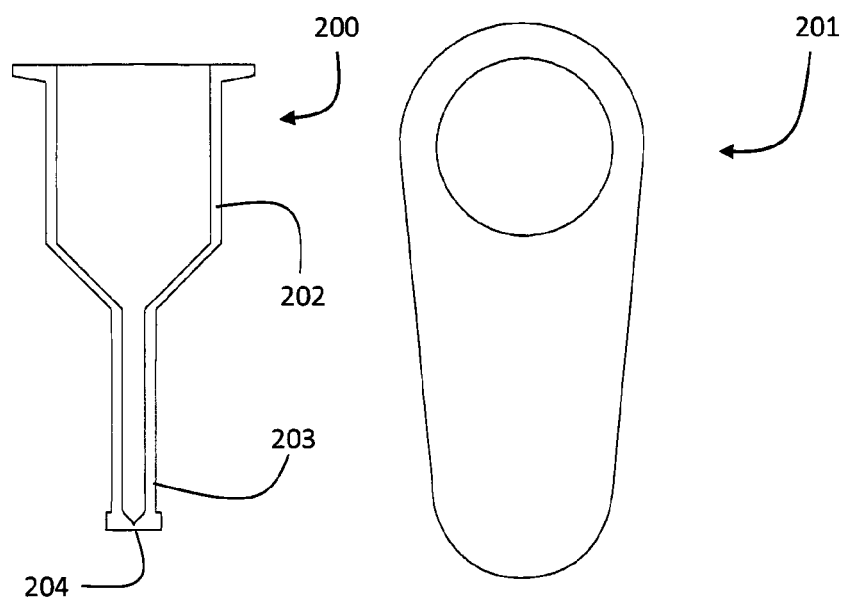
Figure 15:
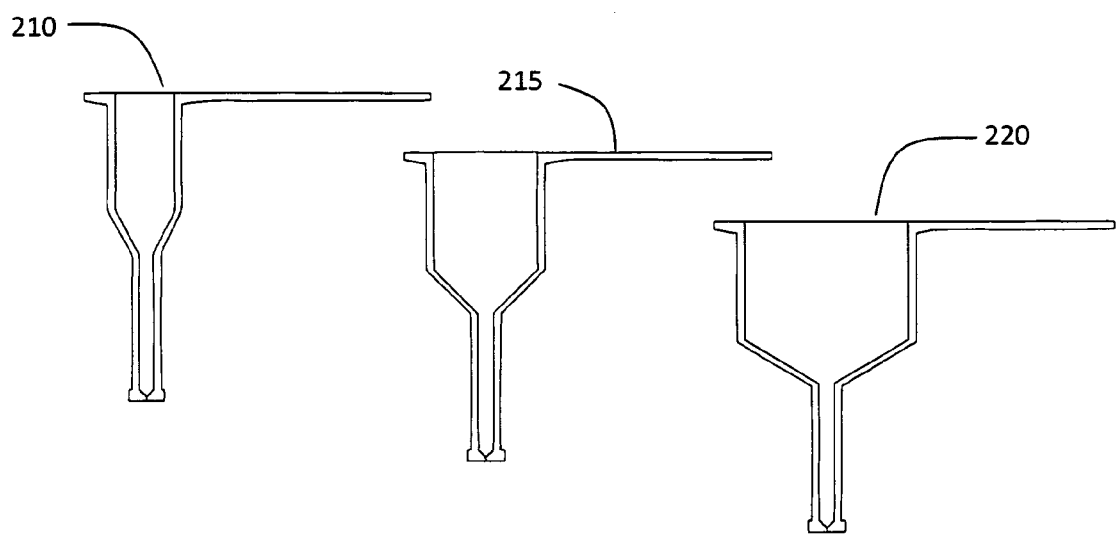
FIG. 15 shows a set having a range of three types of dispensing tip.

FIG. 13 shows an alternative tip, 190, having a reservoir 191, a fluid channel 192, an orifice 193, and a handle 194. FIG. 14 shows a tip 200 for use with a separate handle 201, and having a reservoir 202, a channel 203, and an orifice 204. FIG. 15 shows that a range of different sizes of reservoir may be used in the one apparatus, in this case tips 210, 215 and 220.

Figure 16:
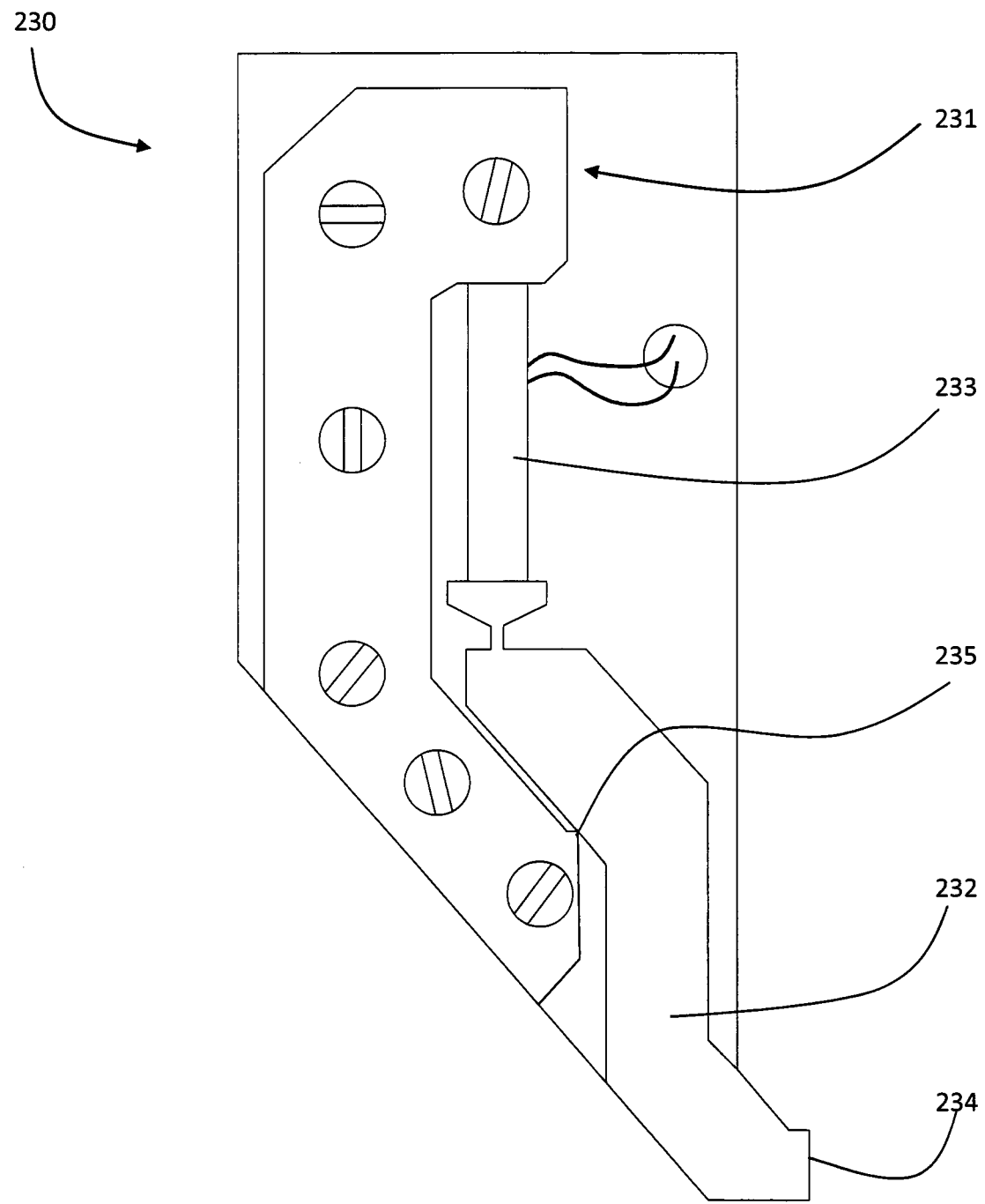
FIG. 16 shows an alternative head actuator assembly arrangement using mechanical amplification of a piezo actuator.

FIG. 16 shows a mechanism 230 for mechanical amplification in an actuator assembly. Piezo amplifier arrangements are discussed in U.S. Pat. No. 4,647,808.

The mechanism 230 is designed to give a clearance of approx 45° around the tip. It has a rigid frame 231 and a lever arm 232. The frame 231 has a relativity large mass relative to the lever arm 232 to ensure that the lever arm 232 causes the pulses to travel into the dispensing tip as opposed to into the frame. The lever arm 232 is light and rigid to ensure a good frequency response. A piezo actuator (in this example a Piezo stack) 233 is connected between the frame 231 and the lever arm 232. The lever arm 232 has and end face 234 which contacts the tip in use to couple the acoustic energy to the tip. Finally, there is a flexure pivot 235 between the frame 231 and the arm 232. As well as amplifying the movement of the piezo actuator, the mechanism facilitates improved mechanical layout of the dispensing head. Amplifying the piezo's movement has the effect of reducing the voltage requirements of the piezo/drive electronics and/or increasing the amount of acoustic energy available to the tip, hence allowing more design freedom of the tip fluid chamber itself. It is also understood that the gain (amplification) of this arrangement may be less than 1.

Figure 17:
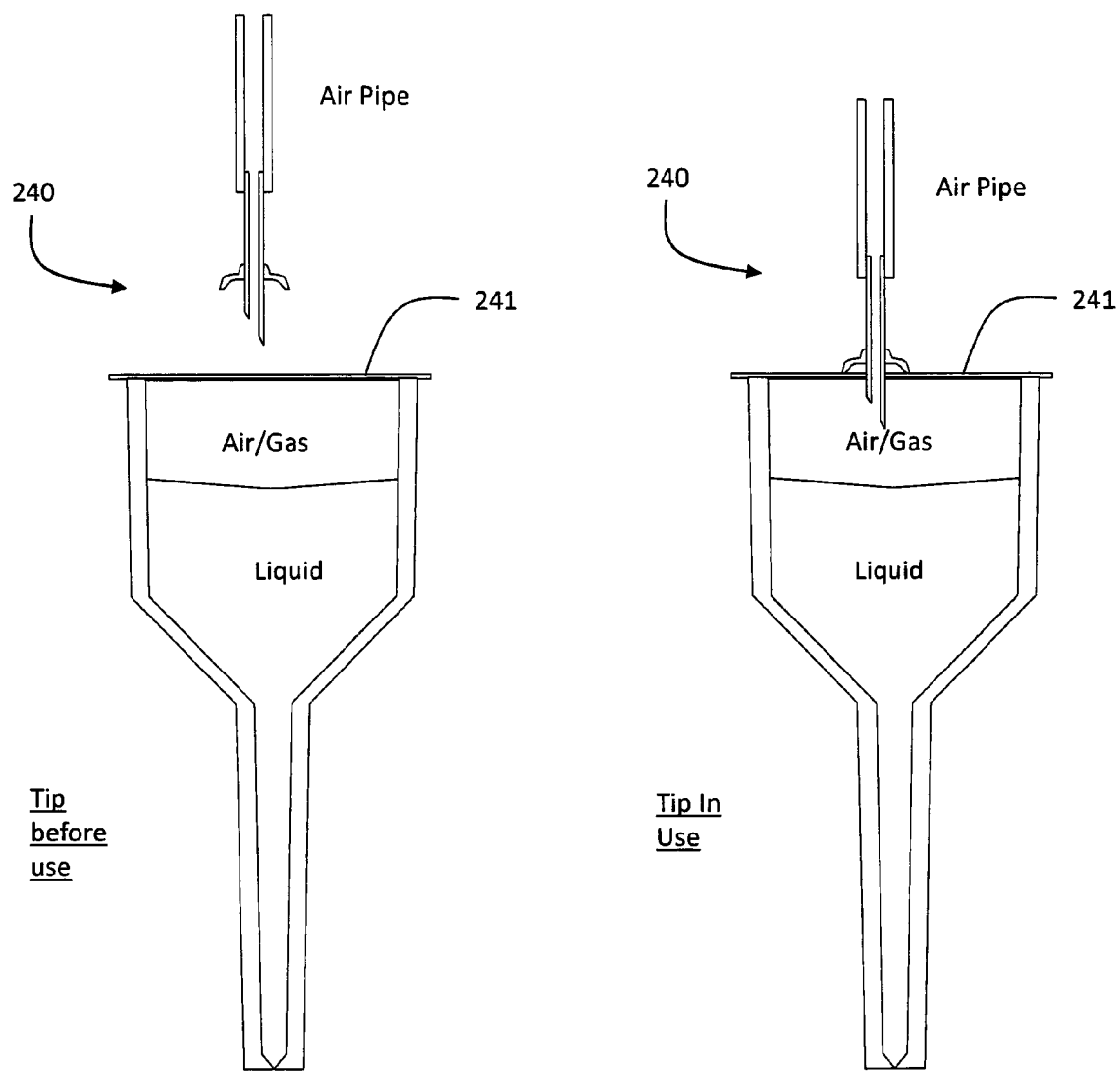
FIG. 17 is a pair of cross-sectional diagrams illustrating an alternative pressure system before and during use.
Figure 18:
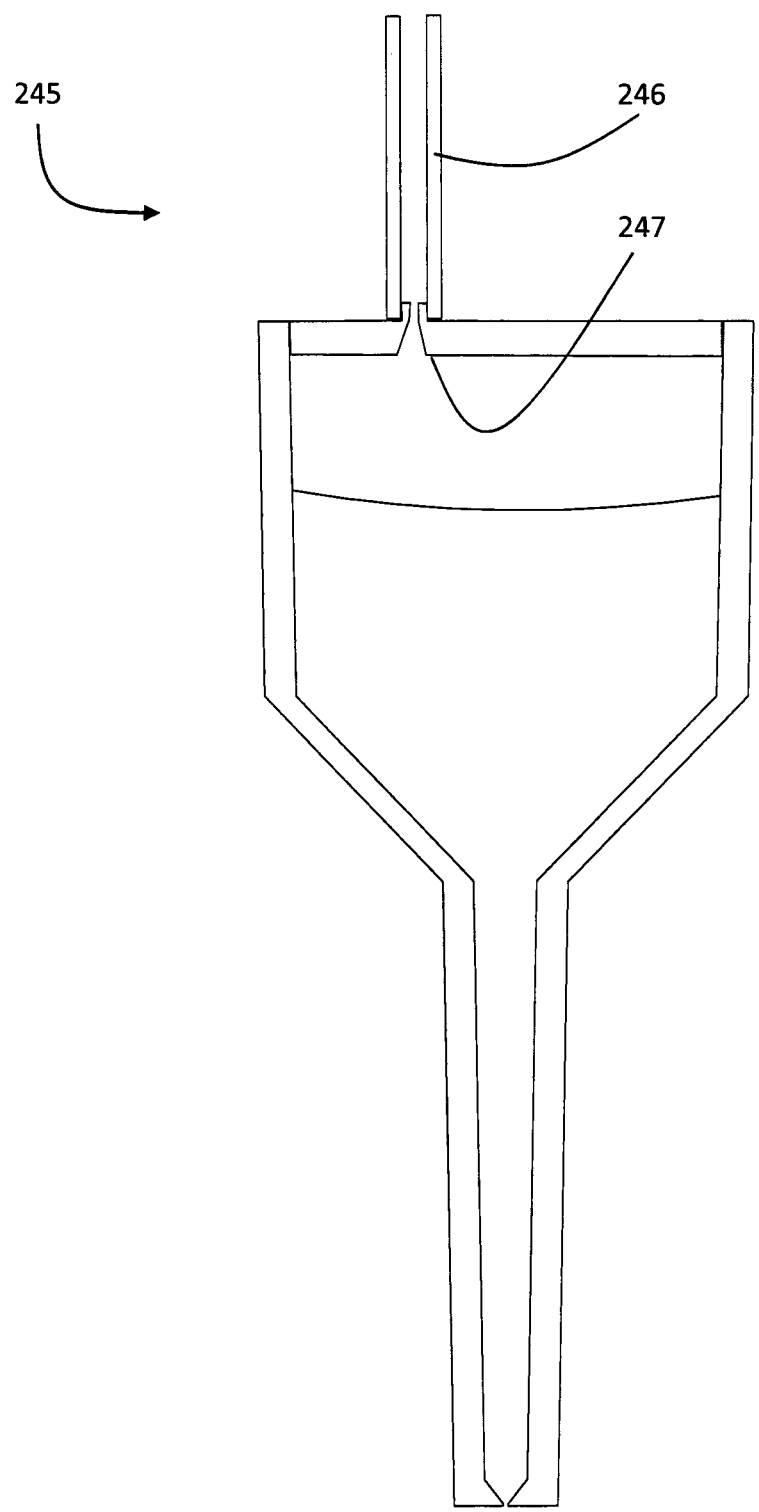
FIG. 18 is a similar view of an alternative dispensing tip and venting means.

Fluidic pressure may be applied to the back end of the tip in a variety of ways. As shown in FIG. 17 a hollow needle 240 punctures a foil lid 241 in the tip. The pressure is then controlled through the needle. This is an alternative way of achieving pressure control. Referring to FIG. 18, an alternative dispensing tip 245 has a pressure control tube 246 connected at a vent 247.

Figure 19:
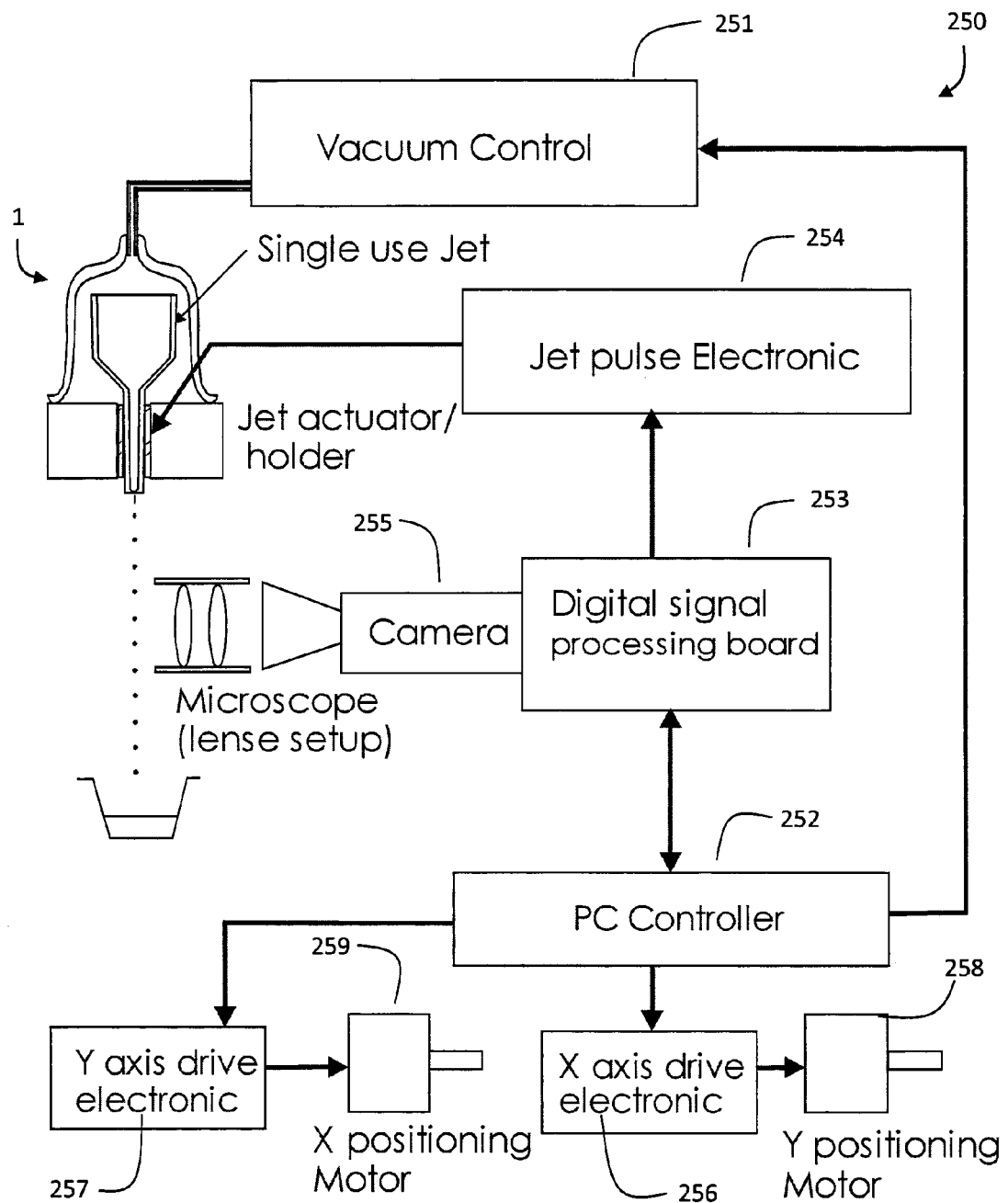
FIG. 19 is a diagram illustrating a dispensing system incorporating the head of FIG. 1.

Referring to FIG. 19 a dispensing system 250 includes the head 1, a vacuum controller 251, a PC controller 252, a digital signal processing board 253, jet pulse electronics 254, a camera 255, X and Y drive electronic circuits 256 and 257, and driving positioning motors 258 and 259 respectively.

The head 1 applies acoustic waves by virtue of a piezo element, this is not a positive displacement pump.

The following are options in various embodiments for feedback and calibration:
a) Camera system views dispensed drops and acts as part of a feedback system on the drop size and volume being dispensed, and/or
b) Detection of satellite drops and feedback to counteract it. When a jet is dispensing, surface tension ideally forms the drops into single spherical drops of the correct size, however in non-ideal conditions there may be 'satellite drops' where multiple drops of various random sizes are created. This is in general an un-stable condition that can be detected and often avoided by adjusting the drive voltage and/or pulse duration and/or pulse waveform shape and/or fluidic pressure and/or frequency, and/or, temperature, etc.
c) Two cameras calculate corrections for, or assessment of, the jet directional inaccuracy, and/or
d) One camera and mirrors are provided to assess directional accuracy, and/or
e) Camera zooms in/out adjustment to focus on the droplet, and/or
f) adjustment of the pulse length, shape and voltage used to generate the drops, and/or
g) Use of a specifically designed optical droplet sensor such as that currently available from Biofluidix™ in place of a camera as part of the feedback system.
h) A camera-based system making decisions based on the physical form of the liquid (shape of the droplet in the early stages of formation) as it leaves the orifice plate.

The system can achieve application of controlled negative pressure at the back (non-orifice end) of the jet to create a slight negative meniscus pressure to aid jetting, and the control of this pressure to compensate for the height of the liquid remaining in the reservoir. In certain situations the system can supply a positive pressure, for example to expel air from the jet. It is also possible that atmospheric pressure would be appropriate for the correct operation of the jet for a given liquid and set of operating parameters.

In one example, during a dispensing cycle the following is the procedure.

1 Insert the tip into the dispensing head (no pressure control).
2 Apply slight negative pressure to avoid dripping of liquid from the tip.
3 Remove the orifice seal (if present).
4 Apply slight positive pressure to ensure there isn't air trapped just inside the orifice. The positive pressure blows this air out with a small amount of liquid, causing liquid to pool on the orifice plate (the flat face with the orifice). This 'pool' begins to form a drop on the orifice plate. When the drop begins to form, as observed by the camera go to step 5.
5. Apply slight negative pressure to allow the pool to retract through the orifice back into the tip.
6 Start applying pulses to the actuator element(s).
7 Wait for droplets to appear.
8 Start running a pressure stabilisation function to maintain continuous satellite-free jetting of droplets, by analysing the droplet stream and making adjustments to the pressure (and possibly other variables such as drive voltage and/or pulse duration and/or back pressure and/or frequency).

9 Stop jetting when the correct number of drops have been dispensed.

The controller 252 causes the actuator to apply controlled pressure pulses of the correct amplitude, duration and shape, to the dispensing tip, to reduce the effects of manufacturing tolerances, and insertion variability.

The system may include a seal or wiper that wipes the jet clean as it is being inserted into the machine. There may be a cleaning cycle to clean/unblock the orifice (e.g.: wipe; pressurise; wipe; apply vacuum; wipe, test firing of droplets).

In one example of use, in order to dispense a sample the dispenser firstly empties itself of the volume of lower priming liquid. The feedback system detects which liquid is being dispensed. This may involve the modification of the properties of the priming liquids so that they can be easily distinguished, such as by including a colorant.

Once the priming liquid is emptied the system is then ready to dispense pico and nano volumes of the sample 32 (FIG. 1). The system 250 (FIG. 19) may know the amount of the sample available, or it may use the feedback system to detect when the sample is used.

Another possibility is to queue or stack different material samples in the dispensing tip itself and separate them with a biologically inert material. This would present advantages in terms of avoiding the necessity to change the dispensing tip to dispense different fluids and potentially reduce the volume of sample material required.

Priming or separation liquids could include biologically inert liquids such as a silicone oil (polymerized siloxanes), or perfluorocarbon (a Teflon-like liquid, colourless, odorless and biologically inert), or with a biologically inert materials which is solid at room temperature (e.g. a low temperature wax which is subsequently heated to bring it into its liquid phase).

Micro-drop dispensers in general can only work with relativity low viscosity liquids, (generally <100 cP). It is well known within the industry that the application of heat to most liquids reduces the viscosity, and will bring a liquid form a viscosity range where it is not dispensable in a micro-drop dispenser, to where it is possible to dispense the liquid.

It has been found, that the application of heat at the orifice region only, is sufficient to alter the viscosity of the liquid being dispensed and will allow droplets to be dispensed, while the remaining volume of fluid, which is not in the orifice region, does not need to be heated.

This method allows for:
a) The dispensing of high viscosity fluids, as their viscosity may be reduced by heating.
b) Additional control of the dispensing parameters which may be useful for liquids which are difficult to dispense.
c) Causing a phase change in a sealing materials (e.g. wax), which may be used to seal the dispensing tip orifice while the material is in the solid phase and subsequently flushed out, or dispensed, prior to dispensing the liquid of interest when the sealing material has been brought into its liquid phase.

Heating only the tip orifice region means that the complete tip does not need to be heated and hence this simplifies the construction of the head actuator assembly, simplifies implementation of the heating means, and in certain cases may prolong the life of some liquids.

Properties of certain liquids may be adversely altered if they are exposed to above ambient temperatures for extended periods of time (e.g. a protein suspension may become denatured if heated excessively). Hence heating only a small region proximal to the orifice may have the result of altering the liquid's viscosity (making it easier to dispense), while not adversely affecting other properties of the liquid, as the liquid is only in the orifice region for a short period of time while it is being dispensed.

Referring again to FIG. 3 the shape of the reservoir 20 was chosen to cover the typical volume commonly used by pipette dispensing devices (about 90 µl). It is envisaged that in other embodiments different convenient reservoir sizes and shapes could be used. It is noted that if the core of the reservoir is sufficiently small the capillary forces can better retain the liquid to prevent it from leaking out through the orifice 4 in the absence of pressure stabilisation. The capillary force is proportional to the contact length around the edge of the liquid, which in turn is proportional to the diameter of the tube, while the weight of the liquid column is proportional to the square of the tube's diameter, so the height of liquid drawn by capillary action decreases quickly as the diameter of the tube increases.

The section of the fluid chamber 25 leading to the orifice 4 plays an important role in the overall jet performance. This fluid chamber, may for example, contain a restriction (a short section with a reduced cross-sectional area) at some point along the fluid chambers length, which is a well known technique in the industry to improve the dispensers drop generation performance.

Figure 20:
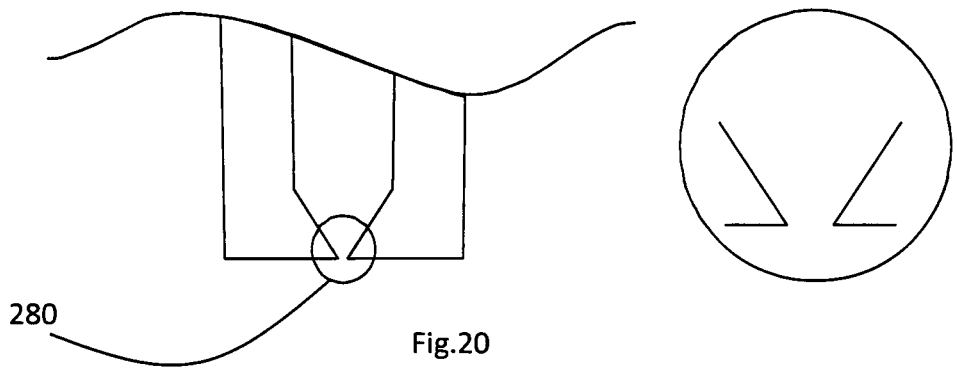
FIGS. 20 to 22 are detailed cross-sectional views showing alternative configurations of a dispensing tip orifice.
Figure 21:
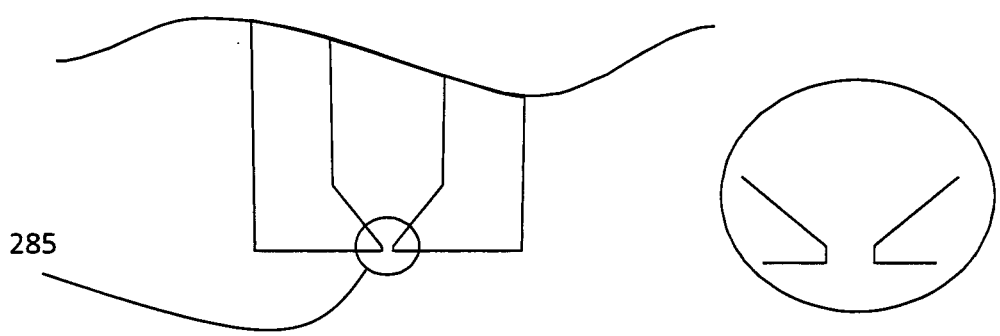
Figure 22:
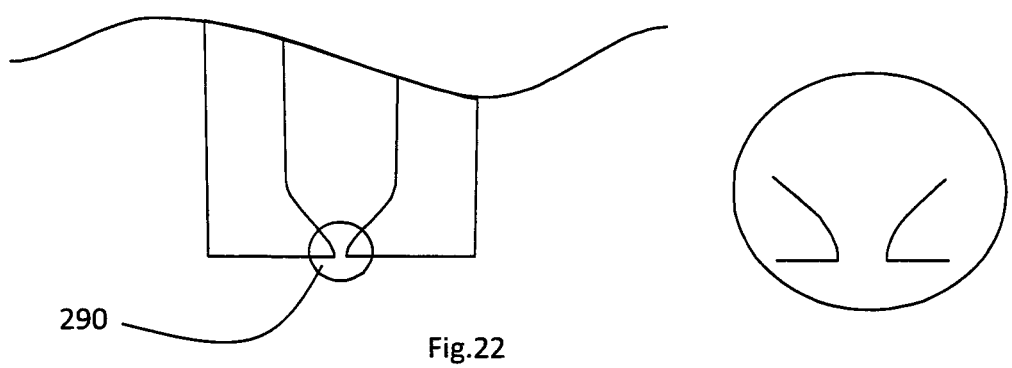

FIGS. 20 to 22 illustrate three different orifice designs.

FIG. 20 shows an acutely angled orifice 280. This has the advantage of having a low fluid impedance, allowing the jet to operate with a lower amplitude of voltage applied to the actuator(s). It is also less prone to clogging (with wanted or un-wanted particles) than other designs because of the low aspect ratio of the final section. However, the orifice of this jet is very delicate because of the very thin sharp edge used to form the orifice itself. With this arrangement the directionality of the drops produced may be poor in some applications.

FIG. 21 shows an orifice 285 which has a straight section leading to the aperture. This arrangement has a higher fluid impedance and thus requires more applied energy to eject a drop. This arrangement is more prone to clogging, and so it may not be suitable for some applications in which the dispensed liquid includes particles. However, directionality of the drops ejected is generally increased and is generally more consistent.

FIG. 22 shows the preferred embodiment, 290, which is a compromise between 280 and 285 above. It has a relatively low fluid impedance, because of its very short straight section and the smooth transition from inner diameter to orifice. There is good directionality because of a short straight section. There is reasonable resistance to clogging because of high aspect ratio of narrow section. The orifice design is less fragile, which should help the manufacturing process.

It is well understood in the industry that the build up of liquid at the orifice surface can cause drops to be ejected at an unwanted angle and in extreme cases can cause the dispenser to not function at all. It is also well known that the application of anti-wetting coatings, or treatments, to the orifice surface of a micro-drop dispenser reduces this problematic build up of liquid around the orifice. In a similar fashion, control of the wettability of the internal wetted surfaces of the tip is useful.

There are many treatments and coatings available for different orifice and or tip materials, including fluoropolymer-based coatings and plasma treatment. It is also understood that if the tip is made of plastic (preferred embodiment) that the type of the plastic can be chosen to control the wetting properties of the tip. Also, it is possible to coat, or treat, the inside surfaces of the dispensing tip to control its wettability as well. In general hydrophobic and hydrophilic coatings are used to control the wettability of surfaces.

The ability to choose the wettability of the orifice surface, and the internal surfaces of the tip independently of each other presents the possibility to design the dispensing tip for use with a particular liquid.

Material Selection and Wall Thickness of Chamber

The material chosen for the preferred embodiment is Polypropylene (PP) for the following reasons:

Physical properties, hardness, elasticity, ductility, and wetting angle.

General acceptance in the pipetting industry (many pipette tips at present are made from PP).

Transparency (for easy diagnosis, checking for air bubbles).

Other mouldable elastolomer/polymer materials could be used for the manufacture of the tip, and PTFE or other additives could be added to control the hardness, elasticity and wetting angles of the tip. It is also feasible to form the dispensing tip from glass, quartz or a metallic material, or a combination thereof; however a plastic material is preferred due to the ease of manufacture and the low cost.

By applying the appropriate voltage pulse to the piezo actuator(s), the actuators are caused to deform. This deformation may be minuscule. However, this minuscule deformation can create a pressure wave. This pressure wave may then be directed to propagate through the walls of a container in which a liquid is held. If the liquid container is of the appropriate design, and contains an orifice (for example a round orifice, circa. 20 µm to 200 µm in diameter), then the pressure wave can be used to deform the meniscus present at the orifice of the liquid container. The pressure wave can be used to deform the meniscus, such that a small liquid column leaves the orifice, breaks off and forms a droplet. This droplet may then fly freely through the air.

The size of droplet ejected, for any particular droplet ejector (jet), is primarily determined by the orifice/aperture size and secondarily by the drive voltages (drive levels and pulse waveform shape) used for drop ejection. Droplets produced by a jet are nominally the same diameter as the orifice/aperture itself. The smallest drop possible tends to be about half the diameter of the orifice, the largest is about twice the diameter of the orifice. The width of this 'band of operation' differs for liquids of different jetting characteristics e.g.: viscosity, and wetting angle. The range in drop size ejected for a given orifice diameter, and liquid, is primarily a function of the drive pulse delivered to the piezo actuator.

If the drive voltage is too low the drop won't clear (break) the meniscus. At too high a drive level, stable drop ejection stops and satellite drops are produced.

Small Drops

The smaller the droplet the more it is affected by:
a) Electric fields
b) Brownian motion
c) Relaxation time constant (the smaller the drop the shorter time it will travel at high speed)
d) Terminal velocity (lower for smaller drops)

As a result, droplets of less than 10 µm in diameter are difficult to position due to their small mass. They 'couple' themselves to local air/gas flow, very shortly after leaving the jet, they will also be pulled easily by electrostatic forces. They tend to appear as a stream of powder that drifts with any air flow, rather than a well-defined direct-able jet of liquid drops.

The smaller the droplet/orifice size also means that the jet will be more sensitive to clogging due to particles (wanted or unwanted) in the liquid.

In a preferred embodiment the jet orifice is moulded in plastics material, the smaller the orifice size the more difficult it is to mould the jet orifice. A tolerance of +/−5 µm will have a much greater effect on a 20 µm orifice than on a 100 µm orifice.

Finally, the optical feedback system providing feedback of the drop size has a particular resolution and processing power. The smaller the drop, the more magnification is needed for a particular resolution camera to keep the resolution of the feedback system the same. Increased magnification reduces the size of the point (window) in space in which the drop has to be for an image to be captured. This reduced window size can create a number of problems:

a) Droplet is left or right of the capture window (error in 'x' caused by miss-directed jet);
b) Droplet is above or below the capture window (error in 'z' caused by miss-timing of capture or pulse velocity jitter);
c) Droplet is out of focus (error in 'y' caused by miss-directed jet).

Large Drops

Orifice sizes of 100 µm and above are prone to suffer from air ingestion and pressure differential problems. The bigger the orifice size, the lower the differential pressure that is necessary for the liquid to break the meniscus (to either leak liquid or ingest air). Also, the drive amplitude (amount of piezo movement) required to eject a drop increases approximately on a square law with orifice diameter. It is desirable to keep the drive amplitude as low as possible (for example below 48 volts, in order to avoid a potential electrical shock hazard).

Aperture Size and Volumes

Table 1

Table 1 provides a list of orifice sizes and corresponding example drop volumes. It is important to note that the drop volume can vary depending on properties of the liquid being dispensed and on the given apparatus configuration.

TABLE 1

| Orifice (diameter if circular) | Cross sectional area (mm$^2$) | Drop Volume |
| --- | --- | --- |
| 20 µm | 0.000314 | 8 pl |
| 30 µm | 0.000707 | 14 pl |
| 40 µm | 0.001257 | 34 pl |
| 50 µm | 0.001963 | 65 pl |
| 60 µm | 0.002827 | 113 pl |
| 70 µm | 0.003848 | 179 pl |
| 80 µm | 0.005027 | 268 pl |
| 90 µm | 0.006362 | 382 pl |
| 100 µm | 0.007854 | 524 pl |
| 110 µm | 0.009503 | 697 pl |

In one embodiment, a preferred orifice size of between 60 µm and 90 µm was used, yielding a drop size of approximately 200 pl, depending on the drive pulse used. With this drop size, it is anticipated that an overall volumetric accuracy of +/−5% is easily achievable on dispensed volumes greater than 5 nl.

An advantage of the invention is its ability to easily generate nano and pico liter volumes of biomaterial from initial volumes in the micro and nano liter range while completely mitigating the risk of cross-contamination, or the need to clean or flush the dispensing tip, by using changeable tips which may if required be disposable (single use). Conventional prior-art piezo dispensing systems have the piezo actuation element bonded to the liquid containing glass capillary tube. This conventional prior-art configuration requires that the dispensing head is cleaned or flushed through with a cleaning fluid between the dispensing of different fluids in order to avoid carry over of cross-contamination between different fluids. These prior-art dispensing heads are expensive as the capillary tube terminating in an orifice is intimately bonded to the actuation element, which makes it uneconomical for them to be disposed of. The invention finds application in, inter alia, biomedical research in academia and industry, mass-production of biomedical products, clinical diagnosis, DNA amplification and protein and antibody micro-array generation.

Another embodiment of the dispensing apparatus and tip is such that the dispensing tip is fed with the liquid to be dispensed via a tube extending from a larger reservoir (e.g. 0.5 liters or larger). In this configuration the back pressure experienced at the meniscus of the dispensing tip orifice may be controlled by adjusting the height of the top of the liquid in the larger reservoir relative to the height of the orifice. In such a configuration the dispensing system may be run for extended periods of time on a single fill of the larger reservoir which feeds the dispensing tip via a liquid carrying conduit, which may be, for example, be in the form of a tube or gallery.

The system is capable of dispensing volumes in the pico and nano liter range, unlike pipettes. It utilises virtually all the sample material and does not require a significant dead volume of liquid to either prime the dispensing tip or remain in the dispensing tip after dispensing has ceased. It is very accurate, reproducible and controllable even at nano and pico volumes. It offers the potential for disposable (single-use) tips to completely avoid the risk of cross contamination between successive liquids. It provides a simple and flexible means of manipulating sub-µl volumes of liquid. It offers the possibility to run a greater number of tests on a given sample volume. It allows one to create one's own protocols at a pico and nano volume level and thus potentially derive more tests than from diagnostic kits currently available.

The invention is not limited to the embodiments described but may be varied in construction and detail. For example, there may be a cast/moulded/machined profile on the inside bore of the piezo element or intermediate material, which may be cone-shaped. Instead of a funnel shape the tip may be cone-shaped or in the configuration of a straight tube terminating at an orifice. An alternative embodiment uses a liquid chamber which is completely conical from the orifice plate to the top (where a lid could be included).

In an alternative embodiment, the system forms part of an automated system. The liquid cartridges/containers do not require a dedicated active element (e.g. piezoelectric device). In such a case, the liquid cartridge/container is fashioned in a manner where one or more nozzles with suitable orifices (as described previously) can be inserted into the actuation element(s), which acts as an actuator to dispense the liquid. The cartridge is in its function and operation similar to the hitherto described dispensing system. The embodiment of the cartridge may be such that it contains a larger quantity of liquid than might be currently considered appropriate for biomedical or industrial applications, due to the possibility to implement a low cost storage, use and reuse model.

The dispenser tips can be stored at low temperatures such as: −20° C. and −80° C., with a liquid present in them and subsequently thawed before they are used or reused.

It is common practise in bio-labs to store bio-fluid at these low temperatures. One can load the tip with a bio-fluid, dispense what is required and then freeze the dispensing tip containing the remaining un-dispensed liquid until it is needed. If one freezes a glass/quartz dispenser with liquid in it, then the expansion of the fluid may crack the dispenser, or damage the orifice rendering it unusable. However if the dispensing tip is composed of plastics material then it will again work fine after thawing out and is not damaged by the freezing/thawing cycle despite having contained a fluid in it. This is a significant advantage to the herein disclosed technology which is over and above the prior state-of-the-art.

It is envisaged that a gel material may be used to couple the acoustic energy into the dispenser tip and still have the tip removable, not bonded with any form of permanent cement or adhesive to the actuation element/assembly, but removable. Also, it is envisaged that the tip may not include a step and upper reservoir. It may instead be in the form of a tube. Also, the tip may be fed with a supply of liquid from a separate reservoir. Also, the tip may have a stepped configuration with ever smaller volumes separated by steps towards the orifice.

The dispensing apparatus is further capable of operating in a mode whereby positive back pressure is applied to liquid in the tip in order to create a continuous flow, or stream, of liquid from the orifice. The actuator assembly may then be used to apply acoustic energy to the tip in order to break the stream into drops. Advantage of this mode of operation include the possibility to exchange the low cost tip if there is a blockage and in addition this mode of operation is potentially capable of delivering larger volumes of liquid in a shorter time period.

The invention is not limited to the embodiments described, but may be varied in construction and detail. For example, instead of a piezo element, the actuator element may be another form of electro-acoustic transducer.

The invention claimed is:

1. A dispensing apparatus for dispensing droplets, the apparatus comprising:
   a dispensing tip having a wall defining a fluid passage with an orifice, said wall having an outer surface,
   an actuator assembly comprising an actuator element and being arranged to engage with the wall of the tip and to disengage from the wall of the tip at said outer surface,
   wherein said orifice has a cross sectional area in the range of 0.00002 mm$^2$ to 0.03 mm$^2$, and
   wherein the actuator is configured to, when engaged, apply a static mechanical pressure against the tip, said static mechanical pressure being a bias force upon which the actuator deforms to propagate a pressure wave through said wall to couple acoustic energy to liquid in the fluid passage to eject said liquid through the orifice as a droplet.

2. The dispensing apparatus as claimed in claim 1, wherein the actuator assembly includes one or more piezo elements.

3. The dispensing apparatus as claimed in claim 2, wherein the piezo elements are in the form of piezo stacks.

4. The dispensing apparatus as claimed in claim 1, wherein the actuator assembly comprises an interface for contacting the dispensing tip and for transferring acoustic energy from the actuator element to the tip.

5. The dispensing apparatus as claimed in claim 1, wherein the actuator assembly comprises an inertial mass for the actuator element to act against in order to couple pressure waves into the dispensing tip.

6. The dispensing apparatus as claimed in claim 1, wherein the actuator assembly comprises a mechanism for amplifying actuator element movement.

7. The dispensing apparatus as claimed in claim 1, wherein the actuator assembly comprises a mechanism for amplifying actuator element movement; and wherein said mechanism comprises a base and a pivoting link arm one end of which is acted upon by the actuator element and the other end of which has a face for engagement with the tip.

8. The dispensing apparatus as claimed in claim 1, wherein the actuator assembly is adapted to provide controlled heating in the region of the orifice only.

9. The dispensing apparatus as claimed in claim 1, wherein the dispensing tip is adapted for storage of liquid before dispensing.

10. The dispensing apparatus as claimed in claim 1, wherein the dispensing tip is in a funnel configuration, having an upper reservoir and a lower liquid-containing portion having the orifice.

11. The dispensing apparatus as claimed in claim 1, wherein the inner surface of the tip at the orifice is funnel-shaped, extending inwardly and downwardly, and bending downwardly to a smaller angle to axial at the orifice.

12. The dispensing apparatus as claimed in claim 1, wherein the dispensing tip further comprises a means of venting and connection to a pressure control system; and/or the dispensing tip has a membrane which may be punctured for use; and/or the material of the dispensing tip is polypropylene.

13. The dispensing apparatus as claimed in claim 1, wherein the apparatus further comprises a sensor arranged to sense liquid dispensing from the dispensing tip, a controller, and feedback means in the controller for dynamically controlling the actuator assembly and/or liquid pressure, and/or liquid temperature, in response to sensing of liquid dispensing.

14. The dispensing apparatus as claimed in claim 1, wherein the system is a biomedical liquid dispensing system.

15. The dispensing apparatus as claimed in claim 1, wherein the apparatus further comprises means to apply a positive back pressure to space within the tip to provide a continuous flow of liquid from the orifice, and the actuator assembly is adapted to apply acoustic energy to break said stream.

16. The dispensing apparatus as claimed in claim 1, wherein the controller is adapted to control the apparatus with the steps of applying:
- negative liquid back pressure to prevent dripping,
- positive liquid back pressure to blow out a small quantity of liquid,
- negative liquid back pressure, and
- acoustic energy pulses to the dispensing tip to create pressure waves for droplet dispensing.

17. A liquid dispensing method performed with a dispensing apparatus comprising:
- a dispensing tip having a wall defining a fluid passage with an orifice and having an outer surface,
- an actuator assembly comprising an actuator element and being arranged to engage with the wall of the tip and disengage from the wall of the tip,
- wherein said orifice has a cross sectional area in the range of 0,00002 mm$^2$ to 0.03 mm$^2$, the method comprising the steps of:
- providing a liquid in the dispensing tip and operating the actuator assembly to cause drops to exit the dispensing tip orifice, in which the actuator assembly applies a static mechanical pressure against said tip outer surface, said static mechanical pressure being a bias force upon which the actuator deforms to propagate a pressure wave through said wall to couple acoustic energy to liquid in the fluid passage to eject said liquid through the orifice as a droplet.

18. The method as claimed in claim 17, wherein a primer liquid which is immiscible with a liquid of interest is contained in the tip.

* * * * *